United States Patent [19]

Ollivier

[11] Patent Number: 6,045,664

[45] Date of Patent: Apr. 4, 2000

[54] PROCESS FOR THE PHOTOCHEMICAL SULPHOCHLORINATION OF GASEOUS ALKANES

[75] Inventor: Jean Ollivier, Arudy, France

[73] Assignee: Elf Atochem S.A., France

[21] Appl. No.: 09/295,110

[22] Filed: Apr. 21, 1999

[30] Foreign Application Priority Data

Apr. 21, 1998 [FR] France .................................. 98 04961

[51] Int. Cl.⁷ .................................................. C07C 11/00
[52] U.S. Cl. ................. 204/157.79; 204/157.67
[58] Field of Search ........................ 204/157.76, 157.79, 204/157.78; 568/28; 562/829

[56] References Cited

U.S. PATENT DOCUMENTS

| | | | |
|---|---|---|---|
| 2,174,508 | 9/1939 | Fox | 562/33 |
| 2,193,824 | 3/1940 | Lockwood | 562/829 |
| 2,335,259 | 11/1943 | Calcott | 204/157.79 |
| 2,352,097 | 6/1944 | Herold | 204/157.79 |
| 2,428,733 | 10/1947 | Asigner | 562/829 |
| 2,462,730 | 2/1949 | Detrick | 204/157.79 |
| 2,665,305 | 1/1954 | Cier | 562/33 |
| 2,709,155 | 5/1955 | Cier | 204/157.79 |
| 3,238,255 | 3/1966 | Blackwell | 562/825 |
| 3,419,486 | 12/1968 | Schenk | 204/157.64 |
| 4,242,187 | 12/1980 | Schlecht | 204/157.79 |
| 4,735,747 | 4/1988 | Ollivier et al. . | |
| 4,997,535 | 3/1991 | Tatsumi et al. . | |

FOREIGN PATENT DOCUMENTS

| | | |
|---|---|---|
| 2 246 520 | of 0000 | France . |
| 2 578 841 | of 0000 | France . |
| 2 595 095 | of 0000 | France . |
| 37 08 784 | of 0000 | Germany . |
| P20023 | of 0000 | Germany . |

OTHER PUBLICATIONS

F. Asinger, "Paraffins, Chemistry and Technology", Pergamon Press 1968, p. 520 et seq.
R. Phillips, "Sources and Applications of Ultraviolet Radiation", Academic Press 1983, pp. 264–276.

*Primary Examiner*—Gary Geist
*Assistant Examiner*—Jean F Vollano

[57] ABSTRACT

For manufacturing an alkanesulphonyl chloride by photochemical reaction of an alkane with chlorine and sulphur dioxide, the light source used is a gallium-doped medium-pressure mercury lamp.

8 Claims, 3 Drawing Sheets

PROCESS FOR THE PHOTOCHEMICAL SULPHOCHLORINATION OF GASEOUS ALKANES

FIELD OF THE INVENTION

The present invention concerns the field of alkanesulphonyl chlorides, and relates more particularly to the manufacture of these compounds by photochemical sulphochlorination of gaseous alkanes at ambient temperature.

BACKGROUND OF THE INVENTION

Given the industrial utility of alkanesulphonyl chlorides, in particular methane sulphonyl chloride, the manufacture of these compounds has formed the subject of several processes, consisting in particular in the photochemical sulphochlorination of alkanes with chlorine and sulphur dioxide. Among these known processes, one particularly effective process for the photochemical sulphochlorination of gaseous alkanes at ambient temperature, for example methane, is the one described in Patents FR 2 578 841 and FR 2 595 095.

This process, which essentially consists in reacting an alkane, sulphur dioxide and chlorine gas mixture in the presence of ultra-violet light delivered by a mercury lamp, is characterized in that the mixture contains a strong excess of sulphur dioxide relative to the alkane, and in that liquid sulphur dioxide is injected into the reaction zone in order to keep the temperature of the latter constant. A plant for implementing this process is also described in the aforementioned patents, the content of which is incorporated here by reference.

In comparison with the photochemical processes of the prior art, which are described in the work by F. ASINGER "Paraffins, Chemistry and Technology", Pergamon Press 1968, p. 520 et seq. and in Patent FR 2 246 520, the process in Patents FR 2 578 841 and FR 2 595 095 has the advantage of not requiring the introduction of any foreign product into the reaction medium, and of forming the latter only with its requisite constituents, namely the alkane, sulphur dioxide and chlorine. Furthermore, this process makes it possible to obtain good conversions and satisfactory yields both with respect to the alkane and with respect to chlorine. Moreover, contributing to better absorption of photons by chlorine and the great ease with which the heat of reaction is dissipated, this process leads to excellent quantum efficiencies and avoids any overheating of the reaction medium.

DESCRIPTION OF THE INVENTION

It has now been found that this performance can be improved further by using a gallium-doped mercury lamp as the light source. In comparison with a mercury lamp of equal power, the use of a light source of this type makes it possible to obtain much better reactor productivity, as well as an improvement in the yield and selectivity of the reaction.

The invention therefore relates to a process for the manufacture of alkanesulphonyl chlorides by photochemical reaction of an alkane with chlorine and sulphur dioxide, optionally in the presence of hydrogen chloride, characterized in that the light source used is a gallium-doped medium-pressure mercury lamp.

The process according to the invention more particularly relates to the sulphochlorination of methane, which is the most difficult alkane to sulphochlorinate, but also applies to all alkanes which are gaseous under the chosen temperature and pressure conditions.

Depending on the starting alkane, the proportions of the reactants in the gas mixture subjected to the light radiation can vary between the following limits:

|  | per mole of methane | per mole of $C_2$ or higher alkane |
|---|---|---|
| $SO_2$ | 1 to 12 mol | 7 to 14 mol |
| $Cl_2$ | 0.1 to 1 mol | 0.1 to 1 mol |
| HCl | 0.1 to 0.6 mol | 0 | and are preferably selected as follows:

|  | per mole of methane | per mole of $C_2$ or higher alkane |
|---|---|---|
| $SO_2$ | 5 to 7 mol | 10 to 13 mol |
| $Cl_2$ | 0.7 to 0.9 mol | 0.7 to 0.9 mol |
| HCl | 0.4 to 0.5 mol | 0 |

The operation is preferably carried out at a pressure above atmospheric pressure. This pressure may generally be from 1 to 15 bar relative, and is preferably between 8 and 12 bar relative.

The reaction temperature, generally between 10 and 90° C., depends on the selected working pressure. It is for example about 60° C. in the case of 10 bar absolute and about 80° C. in the case of 15 bar absolute. As in the process described in Patents FR 2 578 841 and FR 2 595 095, the temperature is kept constant by injecting liquid $SO_2$ into the reaction zone.

BRIEF DESCRIPTION OF THE DRAWINGS

The gallium-doped medium-pressure mercury lamps to be used in accordance with the process according to the invention are well known and are described, for example, in chapter 9 of the work by R. Philips entitled "Sources and Applications of Ultraviolet Radiation" Academic Press 1983, p. 264–276, the content of which is incorporated here by reference. Lamps of this type, marketed by the companies HERAEUS, SILITRO/SCAM and PHILIPS, re-emit more than 60% of their light energy in the form of radiation with wavelengths between 400 and 485 nm. Appended FIGS. 1 and 2 respectively show the emission spectrum of a 750 watt medium-pressure mercury lamp and that of a medium-pressure mercury lamp of the same power doped with gallium. The light energy emitted by the medium-pressure mercury lamp (FIG. 1) is distributed in the form of lines between 220 and 750 nm whereas, in the case of the gallium-doped lamp (FIG. 2), the essential part of the emitted energy is concentrated in the region from 400 to 430 nm. Further to a gain in useful light energy efficiency (about 40%), the illumination of the reaction medium with a gallium-doped medium-pressure mercury lamp is much more uniform than with a conventional mercury lamp. This contributes to a reaction initiation which is better distributed through the reaction volume and, by promoting heat transfer, makes it possible to moderate the local overheating connected with the energy of the reaction; better selectivity is therefore observed.

The process according to the invention can be implemented in a plant similar to the one described in Patent FR 2 578 841. A plant of this type, essentially comprising reactant feed means, a photochemical reactor and means for separating the reaction products, is represented by the schematic drawing in appended FIG. 3.

Figure 1:
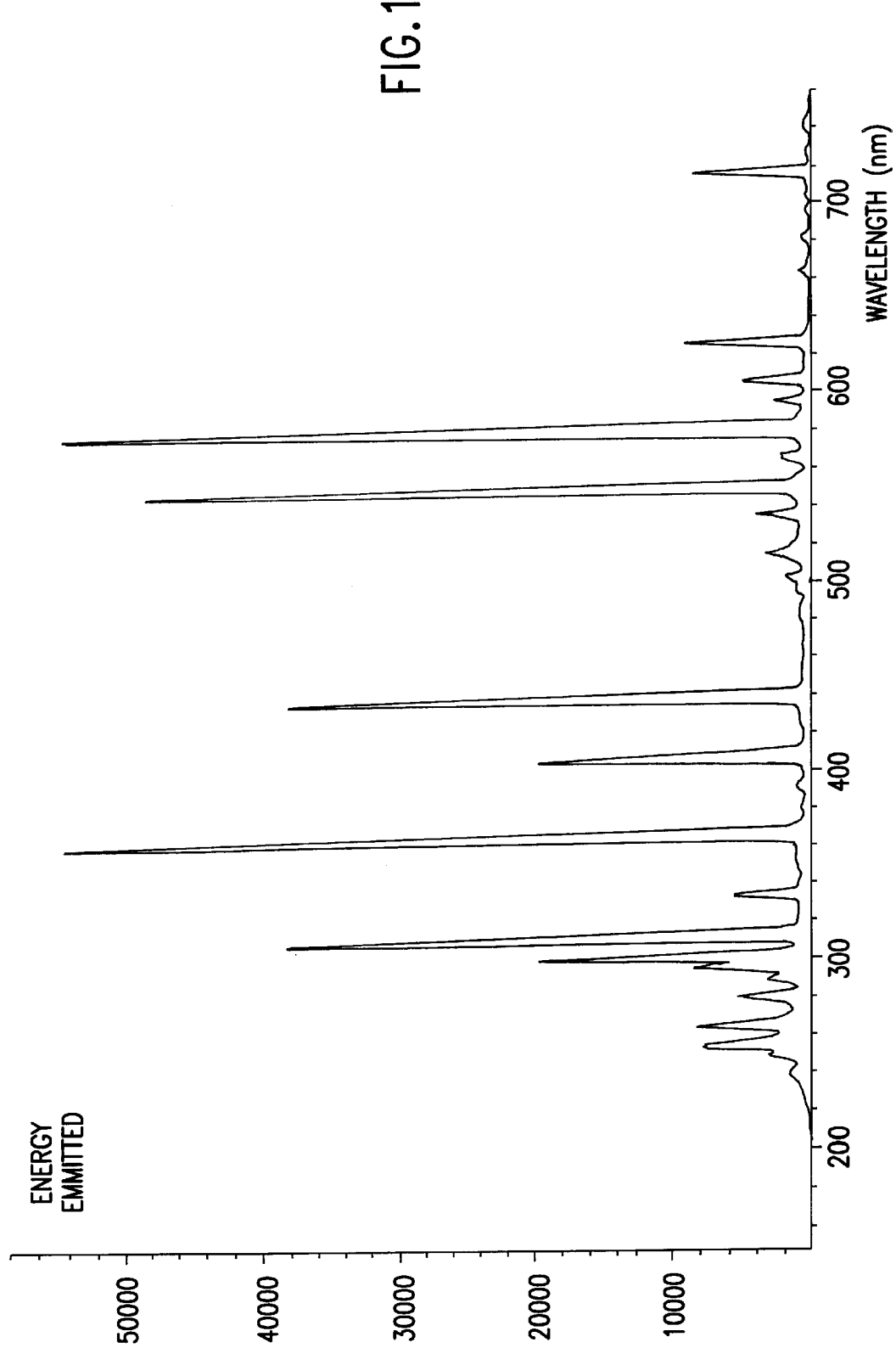
Figure 2:
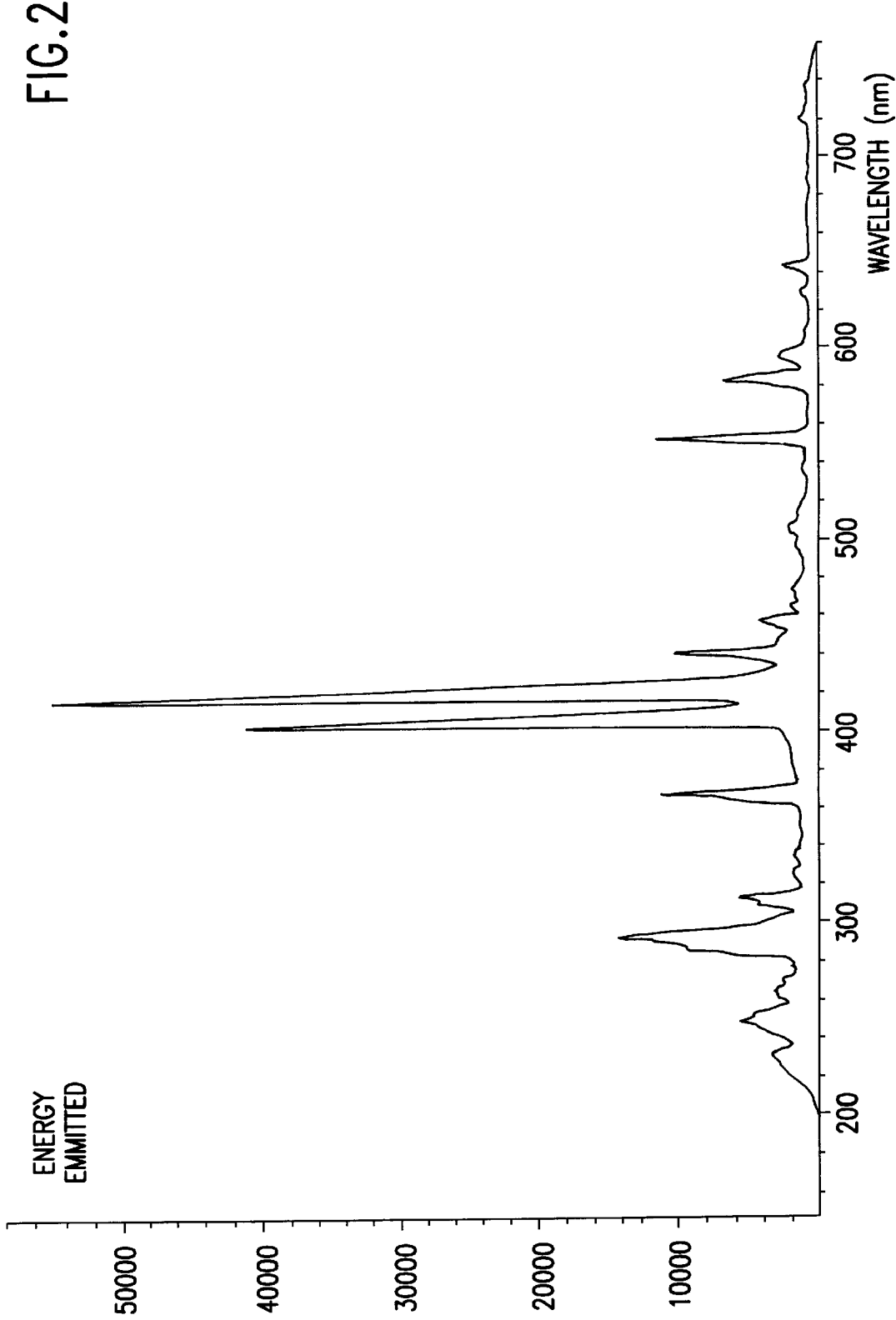
Figure 3:
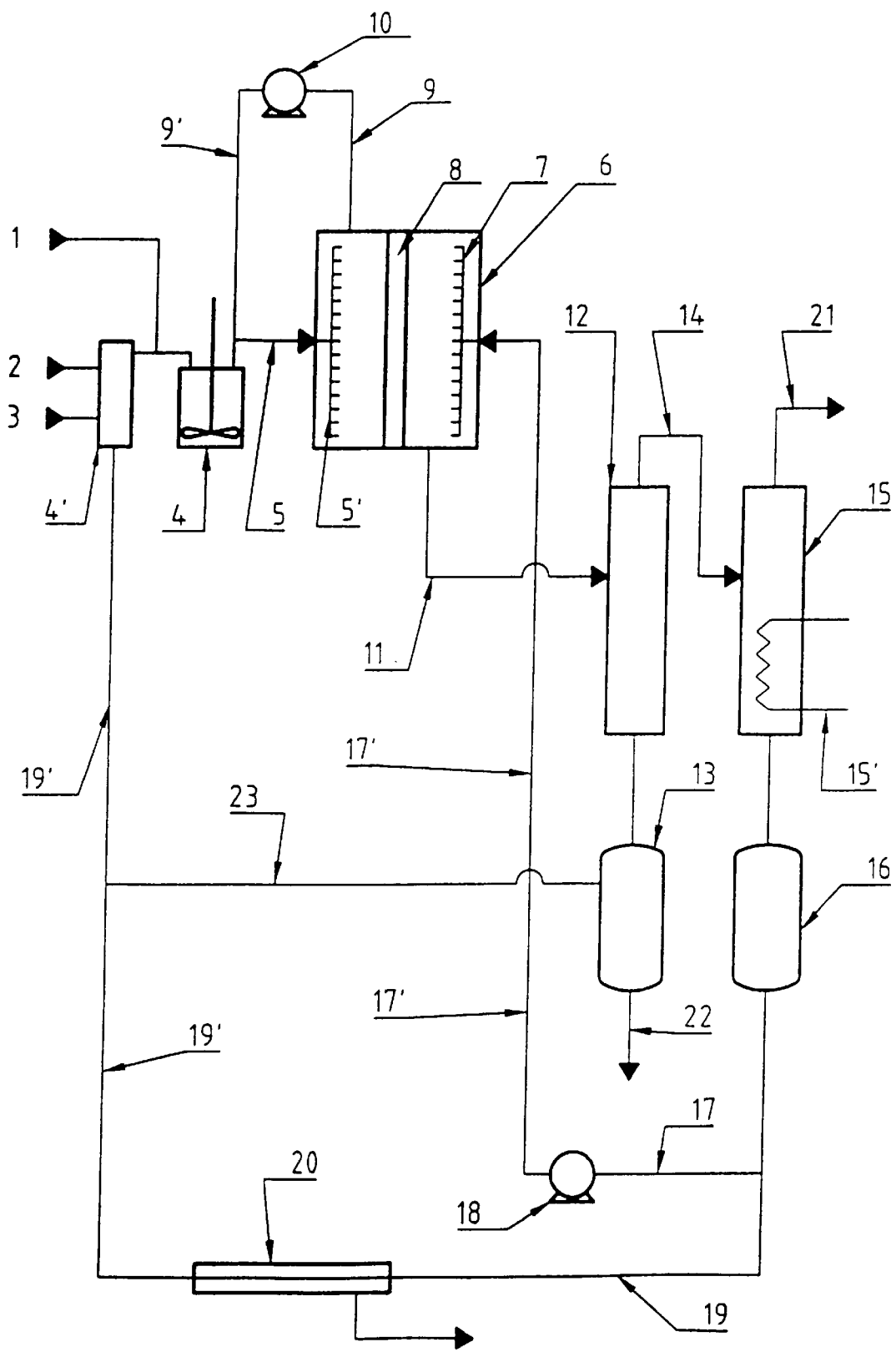

In this drawing, the inlets 1, 2 and 3 are respectively those for the alkane, sulphur dioxide and chlorine which are introduced in the gas state into a mixer 4 provided with a stirrer for rendering the gas mixture uniform; for safety reasons, a $Cl_2$ and $SO_2$ premixer is preferably provided at 4'. The gas mixture passes from the mixer 4 via the duct 5 into the reactor 6, in which it is distributed uniformly by means of a spray pipe 5' having orifices. Another similar spray pipe 7 is also placed over the height of the reactor in order to introduce the liquid $SO_2$ intended for adjusting the temperature. A light source 8 crosses the reactor in a manner known per se. At the top of the reactor 6, a line 9 leads off to a pump 10, making it possible to recycle a fraction of the effluent from the reactor to the line 5 with a view to prediluting the reactants coming from 4. A tube 11 conveys the liquid product formed in the reactor 6 to a separator 12, from where the liquid phase, that is to say the raw alkanesulphonyl chloride, descends into an intermediate tank 13, while the residual gases pass through a duct 14 into a second separator 15. This separator is optionally provided with a cooler 15' for converting the incoming $SO_2$ into the liquid state; the liquid $SO_2$ containing chlorine is recovered from an intermediate tank 16. An $SO_2$ fraction is recycled through the lines 17 and 17' via the pump 18 and the spray pipe 7 into the reactor 6. Another $SO_2$ fraction, coming from 16, passes via the line 19 into the heater 20, and from there via 19' to the feed of the mixer 4.

At the top of the separator 15, the HCl is discharged via the duct 21 to treatment equipment (not shown). From the bottom of the intermediate tank 13, a duct 22 leads off to equipment for purifying the alkanesulphonyl chloride produced (since this equipment does not form the subject-matter of the invention, it is not shown here).

EXAMPLES

The following examples illustrate the invention without limiting it.

Example 1
(Comparative)

In the device described above, methane sulphonyl chloride ($CH_3SO_2Cl$) was prepared by using a medium-pressure mercury lamp as the light source. This 750 watt lamp was placed axially in a 50 liter capacity reactor 6.

For one mol of methane, the gas mixture prepared at 4 contained 6.25 mol of sulphur dioxide, 0.83 mol of chlorine and 0.417 mol of hydrogen chloride. This gas mixture was fed to the reactor at a rate of 5.75 m³ (STP)/hour. The pressure in the reactor being fixed at 9 bar above atmospheric the temperature was adjusted to 65±2° C. by injecting 5.1 kg/h of liquid $SO_2$ by means of the spray pipe 7.

The hourly quantity of raw methane sulphonyl chloride collected after expansion in the tank 13 was 2.5 kg. At atmospheric pressure and at ambient temperature, this raw product had the following composition by weight:

| Constituent | % by weight |
| --- | --- |
| $CH_3SO_2Cl$ | 76.5 |
| $SO_2$ | 18.4 |
| $CH_3Cl$ | 0.5 |
| $CH_2Cl_2$ | 1.5 |
| $CHCl_3$ | 2.0 |
| $CCl_4$ | 0.1 |
| heavy | 1 |

The effluent gas, arriving through 14 in the second separator 15, had the following composition by volume:

| Constituent | % by volume |
| --- | --- |
| $SO_2$ | 83.06 |
| $CH_4$ | 4.33 |
| HCl | 11.1 |
| $Cl_2$ | 1.0 |
| $CH_3Cl$ | 0.5 |

The flow rate of this effluent gas was 6.57 m³ (STP)/hour, and it contained the $SO_2$ gas originating from the evaporation which was used to cool the reaction. In order to collect the sulphur dioxide in the liquid state at a relative pressure of 4 bar, the temperature in the separator 15 was kept below 32° C.

The methane flow rate at the outlet 21 of the separator 15 was 0.27 m³ (STP)/hour. The quantity introduced at 1 was 0.68 m³ (STP)/hour, and the methane conversion was therefore 59%. In the case of chlorine, the conversion rose to 88%.

The results led to the following yields and selectivities with respect to the methane sulphonyl chloride produced:

| | Yield (%) | Selectivity (%) |
| --- | --- | --- |
| for $CH_4$ | 55 | 93 |
| for $Cl_2$ | 70 | 80.6 |

Related to the power of the medium-pressure mercury lamp, the methane sulphonyl chloride productivity was 2.55 kg/kW.

Example 2

In the same equipment as in Example 1, methane sulphonyl chloride was prepared with the conventional mercury lamp being replaced by a gallium-doped lamp of the same electrical power (750 W).

In order to have the same chlorine conversion rate as in Example 1 (88%), the hourly flow rate of the feed gas mixture had to be increased to 6.86 m³ (STP)/hour. The pressure in the reactor being fixed at 9 bar above atmospheric the temperature was adjusted to 65±2° C. by injecting 7.5 kg/h of liquid sulphur dioxide by means of the spray pipe 7.

The hourly quantity of raw methane sulphonyl chloride collected after expansion in the tank 13 was 3.54 kg. At atmospheric pressure and at ambient temperature, this raw product had the following composition by weight:

| Constituent | % by weight |
| --- | --- |
| $CH_3SO_2Cl$ | 76 |
| $SO_2$ | 21.15 |
| $CH_3Cl$ | 0.4 |
| $CH_2Cl_2$ | 0.6 |
| $CHCl_3$ | 0.3 |

-continued

| Constituent | % by weight |
|---|---|
| CCl$_4$ | 0.05 |
| heavy | 1 |

The effluent gas, arriving through 14 in the second separator 15, had the following composition by volume:

| Constituent | % by volume |
|---|---|
| SO$_2$ | 84.6 |
| CH$_4$ | 3.17 |
| HCl | 10.81 |
| Cl$_2$ | 0.92 |
| CH$_3$Cl | 0.5 |

The flow rate of this effluent gas, containing the SO$_2$ gas originating from the evaporation used to cool the reaction, was 8.3 m$^3$ (STP)/hour. In order to collect the sulphur dioxide in the liquid state at a relative pressure of 4 bar, the temperature in the separator 15 was kept below 32° C.

The methane flow rate at the outlet 21 of the separator 15 was 0.26 m$^3$ (STP)/hour. The quantity introduced at 1 was 0.8 m$^3$ (STP)/hour, and the methane conversion was therefore 67%. In the case of chlorine, the conversion rose to 88%.

The results led to the following yields and selectivities with respect to the methane sulphonyl chloride produced:

|  | Yield (%) | Selectivity (%) |
|---|---|---|
| for CH$_4$ | 64.3 | 95.5 |
| for Cl$_2$ | 76 | 86.4 |

Related to the power of the gallium lamp, the methane sulphonyl chloride productivity was 3.58 kg/kW.

The following table summarizes the results of the examples above:

|  | EXAMPLE 1 (Comparative) | EXAMPLE 2 |
|---|---|---|
| Light source | Hg Lamp | Ga Lamp |
| CH$_4$ conversion | 59% | 67% |
| Cl$_2$ conversion | 88% | 88% |
| CH$_3$SO$_2$Cl yield: | | |
| for CH$_4$ | 55% | 64.3% |
| for Cl$_2$ | 70% | 76% |
| CH$_3$SO$_2$Cl selectivity: | | |
| for CH$_4$ | 93% | 95.5% |
| for Cl$_2$ | 80.6% | 86.4% |
| CH$_3$SO$_2$Cl productivity (kg/kw) | 2.55 | 3.58 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. Process of the manufacture of alkanesulphonyl chlorides by photochemical reaction of an alkane with chlorine and sulphur dioxide, optionally in the presence of hydrogen chloride, comprising the light source used is a gallium-doped medium-pressure mercury lamp.

2. Process according to claim 1, wherein the operation is carried out at a pressure of from 1 to 15 bar relative.

3. Process according to claim 1 wherein the reaction temperature is between 10 and 90° centigrade and is kept constant by injecting liquid SO$_2$ into the reaction zone.

4. Process according to claim 1, wherein the gas mixture fed to the reactor comprising 1 to 12 mol of sulphur dioxide, 0.1 to 1 mol of chlorine and 0.1 to 0.6 mol of hydrogen chloride per mole of methane.

5. Process according to claim 4, wherein the gas mixture contains 5 to 7 mol of sulphur dioxide, 0.7 to 0.9 mol of chlorine and 0.4 to 0.5 mol of hydrogen chloride per mole of methane.

6. Process according to claim 1, wherein the alkane contains at least two carbon atoms, the gas mixture fed to the reactor comprising 7 to 14 mol of sulphur dioxide and 0.1 to 1 mol of chlorine per mole of alkane.

7. Process according to claim 6, wherein the amount of sulphur dioxide is from 10 to 13 mol and the amount of chlorine is from 0.7 to 0.9 mol.

8. Process according to claim 2, wherein the pressure is between 8 and 12 bar relative.

* * * * *